(12) United States Patent
Alves De Inda et al.

(10) Patent No.: US 11,399,893 B2
(45) Date of Patent: Aug. 2, 2022

(54) ROTATIONAL POSITION DETERMINATION APPARATUS

(71) Applicant: KONINKLIJKE PHILIPS N.V., Eindhoven (NL)

(72) Inventors: Marcia Alves De Inda, Rosmalen (NL); Wilhelmus Petrus Maria Van Der Linden, Schindel (NL); Maya Ella Barley, Watford (GB); Alessandro Guido Radaelli, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 171 days.

(21) Appl. No.: 16/926,910

(22) Filed: Jul. 13, 2020

(65) Prior Publication Data
US 2020/0337778 A1    Oct. 29, 2020

Related U.S. Application Data

(62) Division of application No. 14/117,389, filed as application No. PCT/IB2012/052679 on May 29, 2012, now Pat. No. 10,736,696.

(30) Foreign Application Priority Data

Jun. 7, 2011 (EP) ...................................... 1168893

(51) Int. Cl.
*A61B 34/10*        (2016.01)
*A61B 17/00*        (2006.01)
(Continued)

(52) U.S. Cl.
CPC .... *A61B 34/10* (2016.02); *A61B 2017/00455* (2013.01); *A61B 2034/105* (2016.02);
(Continued)

(58) Field of Classification Search
CPC .......... A61B 19/50; A61B 2017/00455; A61B 2034/105; A61B 2034/107; A61B 2034/252; A61B 2090/0811; A61B 34/10
See application file for complete search history.

(56) References Cited

U.S. PATENT DOCUMENTS 6,102,938 A    8/2000    Evans et al.
6,221,090 B1   4/2001    Wilson
(Continued)

FOREIGN PATENT DOCUMENTS

WO    2002086797 A1    10/2002
WO    2002097735 A1    12/2002
(Continued)

OTHER PUBLICATIONS

"A Real Time Interactive Surgical Simulator for Catheter Navigation" Lim et al., Surgical-Assist Systems, Proceedings of SPIE 3262: 4-14 (1998).
(Continued)

*Primary Examiner* — Mark D Remaly

(57) ABSTRACT

A rotational position determination apparatus is configured to determine an entry rotational position, which defines a rotational position of an insertion device like a stent at an entry site, such that a navigation of the insertion device from the entry site to a target site along an inner path results in a rotational position of the insertion device at the target site being equal to a desired target rotational position based on a representation of the inner path and the desired target rotational position. If the insertion device is arranged in the determined entry rotational position at the entry site and then navigated to the target site, it is therefore not necessary to rotate the insertion device at the target site.

5 Claims, 5 Drawing Sheets

(51) Int. Cl.
*A61B 34/00* (2016.01)
*A61B 90/00* (2016.01)

(52) U.S. Cl.
CPC ... *A61B 2034/107* (2016.02); *A61B 2034/252* (2016.02); *A61B 2090/0811* (2016.02)

(56) References Cited

U.S. PATENT DOCUMENTS

| | | |
|---|---|---|
| 7,877,128 B2 | 1/2011 | Schwartz |
| 8,784,435 B2 | 7/2014 | Cooper et al. |
| 2002/0137014 A1 | 9/2002 | Anderson et al. |
| 2004/0054403 A1 | 3/2004 | Israel |
| 2006/0184011 A1 | 8/2006 | Macaulay et al. |
| 2006/0241368 A1 | 10/2006 | Fichtinger |
| 2007/0055361 A1 | 3/2007 | Park |
| 2007/0078325 A1 | 4/2007 | Fuimaono |
| 2007/0249934 A1 | 10/2007 | Aksit et al. |
| 2009/0304245 A1 | 12/2009 | Egger et al. |
| 2010/0036390 A1 | 2/2010 | Gumm |
| 2011/0282351 A1 | 11/2011 | Cooper |
| 2013/0131502 A1 | 5/2013 | Blaivas et al. |
| 2014/0296704 A1 | 10/2014 | Marcia et al. |

FOREIGN PATENT DOCUMENTS

| | | |
|---|---|---|
| WO | 2006093546 A1 | 9/2006 |
| WO | 2010064154 A1 | 6/2010 |
| WO | 2011063511 A1 | 6/2011 |

OTHER PUBLICATIONS

"Remote Manipulation of Guidewire Using A Virtual Reality Device" Fukasaku et al, Interventional Neuroradiology 7: p. 29-34 Dec. 1, 2001.

"Simulation of Guidewire Navigation in Complex Vascular Structures" Guilloux et al, Medical Imaging 2006; Visualizaiton Image-Guided Procedures and Display, 614107 (2006).

"Development of a Training System for Interventional Radiology" Ide et al., Modelling in Medicine and Biology VIII;p. 313-322 (2009).

ROTATIONAL POSITION DETERMINATION APPARATUS

CROSS-REFERENCE TO PRIOR APPLICATIONS

This application a divisional application of U.S. patent application Ser. No. 14/117,389, filed Nov. 13, 2013, which is the U.S. National Phase application under 35 U.S.C. § 371 of International Application Serial No. PCT/IB2012/052679, filed on May 29, 2012, which claims the benefit of European Patent Application Serial No. EP11168893.3, filed on Jun. 7, 2011. These applications are hereby incorporated by reference herein

FIELD OF THE INVENTION

The invention relates to a rotational position determination apparatus, a rotational position determination method and a rotational position determination computer program for determining a rotational position of an insertion device for being inserted into an object at an entry site and for being navigated along an inner path within the object to a target site within the object. The invention relates further to a rotational positioning assistance apparatus and a rotational positioning assistance method for assisting in positioning the insertion device, and a rotational positioning apparatus and a rotational positioning method for positioning the insertion device.

BACKGROUND OF THE INVENTION

US 2009/0304245 A1 discloses a method for a structurally individualized simulation of a wall support element introduced into a section of a tubular structure. Image data of the interior of the section of the tubular structure are provided and a start point and an end point of the section of the tubular structure are determined, wherein between the start point and the end point a lumen and a profile line of the tubular structure are determined. Furthermore, an individual elastic structure model for the section of the tubular structure is identified by adapting a tubular elastic initial model to the section of the tubular structure on the basis of the identified lumen and the profile line, and a tubular elastic wall support element model which is positioned inside the individual structure model is provided. The wall support element model is then virtually and stepwisely expanded, wherein in each expansion step a check for collisions between the wall support element model and the individual structure model is carried out. At the positions where a collision is identified, the wall support element model and the individual structure model are modified at least locally while taking into account the elasticity of the individual structure model.

US 2010/0036390 A1 discloses a method for delivering a stent to a bifurcation of a vessel. A first guidewire is advanced through a body lumen to a first branch of a vessel bifurcation. A second guidewire is advanced through a body lumen to a second branch of the vessel bifurcation. Moreover, a catheter assembly is advanced to the vessel bifurcation along the first guidewire and the second guidewire, wherein the catheter assembly comprises a catheter shaft defining a first guidewire lumen for receiving the first guidewire and a balloon rotatably disposed about the catheter shaft, wherein the balloon is freely rotatable about the first guidewire. The catheter assembly further comprises a tubular member engaged to an external surface of the balloon, wherein the tubular member defines a second guidewire lumen for receiving the second guidewire, and a stent, wherein the stent is disposed about at least a portion of the balloon and the tubular member and wherein the second guidewire passes through at least one opening defined by the stent. The balloon is rotatable about the first guidewire, in order to allow the stent to be arranged in a desired rotational position. For providing this rotation functionality a technically relatively complex construction of the catheter assembly is required.

SUMMARY OF THE INVENTION

It is regarded as being an object of the present invention to provide a rotational position determination apparatus, a rotational position determination method and a rotational position determination computer program for determining a rotational position of an insertion device for being inserted into an object at an entry site and for being navigated along an inner path within the object to a target site within the object, wherein the determination of the rotational position allows to use a technically less complex interventional device for inserting the insertion device. It is a further object of the present invention to provide a rotational positioning assistance apparatus and a rotational positioning assistant method for assisting in positioning the insertion device, and a rotational positioning apparatus and a rotational positioning method for positioning the insertion device, which allow using a technically less complex interventional device for inserting the insertion device.

In a first aspect of the present invention a rotational position determination apparatus for determining a rotational position of an insertion device for being inserted into an object and for being navigated along an inner path within the object from an entry site to a target site within the object is presented, wherein the rotational position determination apparatus comprises:

an inner path providing unit for providing a representation of the inner path within the object, a target rotational position providing unit for providing a desired target rotational position of the insertion device at the target site, an entry rotational position determination unit for determining an entry rotational position, which defines a rotational position of the insertion device at the entry site, such that a navigation of the insertion device from the entry site to the target site along the inner path results in a rotational position of the insertion device at the target site being equal to the desired target rotational position based on the representation of the inner path and the desired target rotational position.

Since the entry rotational position determination unit determines the entry rotational position such that a navigation of the insertion device from the entry site to the target site along the inner path results in a rotational position of the insertion device at the target site being equal to the desired target rotational position based on the representation of the inner path and the desired target rotational position, the insertion device can be arranged at the entry site in the determined entry rotational position such that, after the insertion device has been moved from the entry site to the target site along the inner path, the insertion device is correctly located at the target site in the desired target rotational position. It is therefore not necessary to rotate the insertion device at the target site, i.e. it is not necessary to provide a technically complex interventional device for inserting the insertion device.

In an embodiment, the inner path providing unit is a storing unit, in which the representation of the inner path within the object is stored, wherein the stored inner path can be provided by the storing unit for simulating the navigation of the insertion device from the entry site to the target site. Also the target rotational position providing unit can be a storage unit, in which the desired target rotational position of the insertion device at the target site is stored, wherein the stored desired target rotational position can be retrieved from the storage unit for providing the desired target rotational position.

The object is preferentially a person or an animal, wherein the target site is preferentially located within a vessel like the aorta artery or an organ like the heart.

The insertion device is preferentially a device which is insertable into the object. In particular, the insertion device is an implantable device like a stent. In an embodiment, the insertion device is an endovascular device. For example, the endovascular device is an asymmetric endovascular device like a fenestrated stent, which may be two-legged or which may comprise more legs, or a multi-branched stent. The rotational position determination apparatus allows therefore correctly positioning an endovascular device, without providing the endovascular device or a delivery unit comprising the insertion device for delivering the same with a mechanism for rotating the endovascular device within a person or an animal, in particular, within an organ or a vessel of the person or the animal.

It is preferred that the entry rotational position determination unit is adapted to simulate the navigation of the insertion device from the entry site to the target site based on the representation of the inner path and the desired target rotational position for determining the entry rotational position. However, the entry rotational position determination unit can also be adapted to determine the entry rotational position without performing a simulation. For example, if, in an embodiment, the inner path is relatively straight and has a relatively large diameter such that a rotation of the insertion device is not required while being navigated from the entry site to the target site, the entry rotational position can be determined as being equal to the desired target rotational position, or, if it is known from, for instance, a data base, that a navigation along the actual inner path requires a rotation of the insertion device by a certain known angle, the entry rotational position can be determined based on the provided target rotational position and the certain known angle, without necessarily performing a simulation.

The insertion device can be navigated along the inner path by using a delivery system, wherein the entry rotational position determination unit is adapted to determine the entry rotational position such that the navigation of the insertion device from the entry site to the target site along the representation of the inner path by using the delivery system results in a rotational position of the insertion device at the target site being equal to the desired target rotational position based on the representation of the inner path, the desired target rotational position and the delivery system. The delivery system preferentially comprises a delivery unit and a guidewire, wherein the delivery unit comprises an insertion device, for example, a stent, and is movable along the guidewire for transferring the insertion device from the entry site to the target site. If the insertion device is held by the delivery unit in a fixed spatial relationship, the entry rotational position of the insertion device can be determined by determining an entry rotational position of the delivery unit. If the entry rotational position is determined by simulation, the simulation can consider the functionality and dimensions of the delivery unit for determining the entry rotational position. The delivery unit is, for example, a known delivery unit for delivering the insertion device along the guidewire.

It is further preferred that the rotational position determination apparatus comprises a three-dimensional vessel geometry model providing unit for providing a three-dimensional vessel geometry model representing a vascular network of the object, wherein the inner path providing unit is adapted to determine the inner path by determining a path through the three-dimensional vessel geometry model from the entry site to the target site. The three-dimensional vessel geometry model providing unit is preferentially adapted to generate a three-dimensional image of a vascular network of the object and to segment the three-dimensional image for extracting a three-dimensional vessel geometry model. This allows automatically determining the inner path accurately such that the entry rotational position can reliably be determined.

In a preferred embodiment, the rotational position determination apparatus further comprises a three-dimensional vessel geometry model providing unit representing a vessel configuration at least at the target site, wherein the insertion device is an endovascular device being adapted to fit to the vessel configuration at the target site in at least one rotational position, wherein the target rotational position providing unit is adapted to determine the desired target rotational position such that the endovascular device fits to the vessel configuration at the target site. For example, if the endovascular device is a fenestrated stent, the target rotational position providing unit can be adapted to determine the desired target rotational position of the fenestrated stent such that the apertures of the stent are correctly aligned with, for example, corresponding aortic side branches.

The rotational position determination apparatus preferentially further comprises an inner path element selection unit for selecting an inner path element for being transferred along the inner path based on characteristics of the inner path determined from the representation of the inner path. This allows selecting an inner path element, which is suitable for being used along the respective inner path. In particular, the inner path element selection unit can be adapted to select a delivery system for delivering the insertion device to the target site as the inner path element. For example, the length of the inner path can be provided by an inner path length determination unit for determining the length of the inner path based on the provided representation of the inner path, wherein the inner path element selection unit can be adapted to select guidewires having a length being optimized for the length of the respective inner path. In an embodiment, the inner path element selection unit can comprise a data base, in which assignments between inner path elements and characteristics of the inner path like the length, the maximal diameter, the minimal diameter, the minimal curvature the maximal curvature, et cetera are stored, wherein a suitable inner path element can be selected from the data base based on the assignments. For example, the flexibility of the guidewire can be selected based on the maximal curvature of the inner path.

The rotational position determination apparatus can further comprise an entry path providing unit for providing a representation of an entry path from the outside of the object to an end of the inner path at the entry site, wherein the entry rotational position determination unit is adapted to determine the entry rotational position such that the navigation of the insertion device from the entry site to the target site along the entry path and the inner path results in a rotational position of the insertion device at the target site being equal to the desired target rotational position based on the representation of the entry path, the representation of the inner path and the desired target rotational position. For example, the navigation of the insertion device along the entry path and along the inner path can be simulated based on the representation of the inner path and the representation of the entry path, in order to determine the entry rotational position at the entry site at the outside of the object such that a navigation of the insertion device from the outside of the object at the entry site along the entry path and along the inner path to the target site results in a rotational position of the insertion device at the target site being equal to the desired target rotational position. However, also regarding the entry path the change of the rotational position obtained while navigating the insertion device along the entry path can be determined without performing a simulation. For example, if, in an embodiment, the entry path is relatively straight and has a relatively large diameter such that a rotation of the insertion device is not required while being navigated along the entry path, the change of the rotational position of the insertion device, which is obtained while navigating the insertion device along the entry path, can be zero, or, if it is known from, for instance, a data base, that a navigation along the actual entry path requires a rotation of the insertion device by a certain known angle, the change of the rotational position obtained while navigating the insertion device along the entry path can be determined by using the data base.

The entry path providing unit can be adapted to provide the entry path based on an image of the entry site showing the entry path. For example, the entry path can be provided by an introducer sheath, which has been introduced at the entry site in a person to provide an access to an artery, in particular, an access to the femoral artery. The provided image shows preferentially the introducer sheath and, thus, the entry path. The provided image is, for example, a fluoroscopy image, wherein the introducer sheath preferentially comprises markers visible in the fluoroscopy image such that the entry path is visible in the fluoroscopy image. The entry path providing unit can be adapted to detect the introducer sheath in the fluoroscopy image and to determine the entry path depending on the detected introducer sheath.

In a further aspect of the present invention a rotational positioning assistance apparatus for assisting in positioning an insertion device for being inserted into an object at an entry site and for being navigated along an inner path within the inner object to a target site within the object is presented, wherein the rotational positioning assistance apparatus comprises an indication unit for indicating a desired entry rotational position at the entry site determined by the rotational position determination apparatus.

The rotational positioning assistance apparatus can indicate the correct entry rotational position to a user like a physician, in order to allow the user to correctly arrange the insertion device at the entry site. If the entry rotational position has been determined at the outside of an object, in particular, at the outside of a person, at the entry site by considering the representation of the inner path and the representation of the entry path, the indication unit is adapted to indicate the desired entry rotational position at the outside of the object at the entry site, for example, at the entrance of the entry path.

It is preferred that the indication unit is a display showing the desired entry rotational position.

The rotational positioning assistance apparatus further comprises an actual entry rotational position determination unit for determining an actual entry rotational position of the insertion device at the entry site, and a deviation calculation unit for calculating a deviation between the actual entry rotational position and the desired entry rotational position, wherein the indication unit is adapted to indicate the desired entry rotational position by indicating the deviation. The indication unit is, for example, a display, which can show a text or a graphic for advising the user to rotate the insertion device by an angle representing the calculated deviation.

In a further aspect of the present invention a rotational positioning apparatus for positioning an insertion device for being inserted into an object at an entry site and for being navigated along an inner path within the inner object to a target site within the object is presented, wherein the rotational positioning apparatus comprises a positioning unit for positioning the insertion device at the entry site in an entry rotational position determined by the rotational position determination apparatus. The rotational positioning apparatus can be used for automatically positioning the insertion device at the entry site in the determined entry rotational position.

The positioning unit is preferentially adapted to rotate the insertion device to the entry rotational position. The rotational position determination apparatus is preferentially adapted to determine the entry rotational position with respect to a reference rotational position. The reference rotational position is preferentially also known by the rotational positioning assistance apparatus and/or the rotational positioning apparatus, in order to allow the rotational positioning assistance apparatus and/or the rotational positioning apparatus to indicate the determined entry rotational position and/or to position the insertion device at the entry site in the entry rotational position with respect to the reference rotational position.

In a further aspect of the present invention a rotational position determination method for determining a rotational position of an insertion device for being inserted into an object at an entry site and for being navigated along an inner path within the object to a target site within the object is presented, wherein the rotational position determination method comprises:
  providing a representation of the inner path within the object by an inner path providing unit,
  providing a desired target rotational position of the insertion device at the target site by a target rotational position providing unit,
  determining an entry rotational position, which defines a rotational position of the insertion device at the entry site, such that a navigation of the insertion device from the entry site to the target site along the inner path results in a rotational position of the insertion device at the target site being equal to the desired target rotational position based on the representation of the inner path and the desired target rotational position by an entry rotational position determination unit.

In a further aspect of the present invention a rotational positioning assistance method for assisting in positioning an insertion device for being inserted into an object at an entry site and for being navigated along an inner path within the object to a target site within the object is presented, wherein the rotational positioning assistance method comprises indicating a desired entry rotational position at the entry site, which is determined by the rotational position determination method, by an indication unit.

In a further aspect of the present invention a rotational positioning method for positioning an insertion device for being inserted into an object at an entry site and for being navigated along an inner path within the object to a target site within the object is presented, wherein the rotational positioning method comprises positioning the insertion device at the entry site in an entry rotational position, which is determined by the rotational position determination method, by the rotational positioning apparatus.

In a further aspect of the present invention a computer program for determining a rotational position of an insertion device for being inserted into an object at an entry site and for being navigated along an inner path within the object to a target site within the object is presented, wherein the computer program comprises program code means for causing the rotational position determination apparatus to carry out the steps of the rotational position determination method, when the computer program is run on a computer controlling the rotational position determination apparatus.

It shall be understood that the rotational position determination apparatus, the rotational positioning assistance apparatus, the rotational positioning apparatus, the rotational position determination method, the rotational positioning assistance method, the rotational positioning method and the computer.

These and other aspects of the invention will be apparent from and elucidated with reference to the embodiments described hereinafter.

DETAILED DESCRIPTION OF EMBODIMENTS

Figure 1:
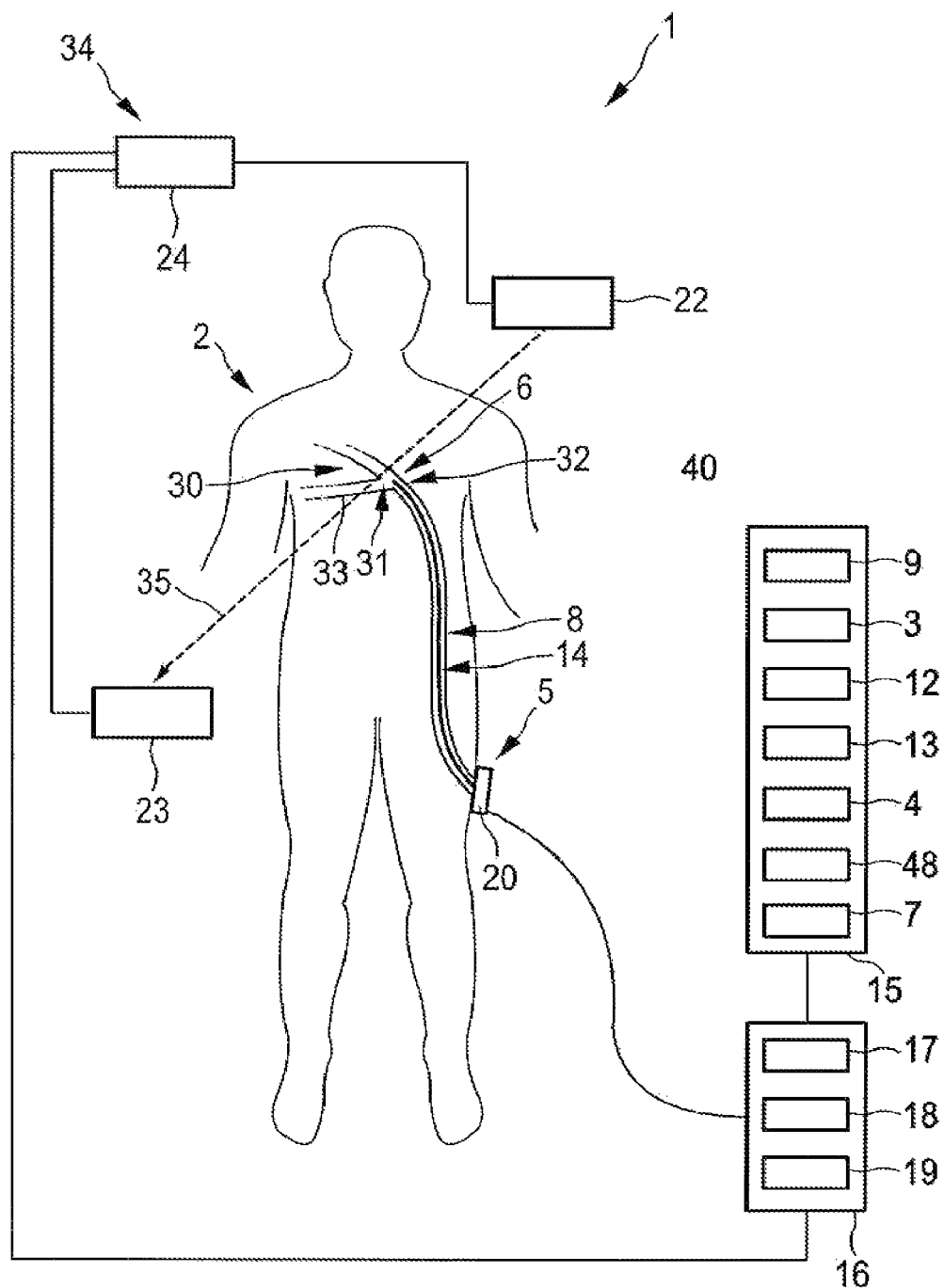
FIG. 1 shows schematically and exemplarily an embodiment of a rotational position determination apparatus, an embodiment of a rotational positioning assistance apparatus and an embodiment of a rotational positioning apparatus being used in an interventional procedure.

FIG. 1 shows schematically and exemplarily an embodiment of a rotational position determination apparatus 15, an embodiment of a rotational positioning assistance apparatus 16 and an embodiment of a rotational positioning apparatus 20, which are used in an interventional procedure, in which an insertion device is inserted into a person 2 at an entry site 5 and navigated along an inner path 8 within the person 2 to a target site 6.

The rotational position determination apparatus 15 is adapted to determine an entry rotational position defining the rotational position of the insertion device at the entry site 5. The rotational position determination apparatus 15 comprises a three-dimensional vessel geometry model providing unit 9 for providing a three-dimensional vessel geometry model representing a vascular network of the person 2. Preferentially, the three dimensional vessel geometry model providing unit 9 is adapted to generate a three-dimensional image of a vascular network of the person 2 and to segment the three-dimensional image for extracting the three-dimensional vessel geometry model. The three-dimensional image is, for example, a computed tomography image, a magnetic resonance image or an image generated by another imaging modality. The three-dimensional vessel geometry model providing unit 9 can also be a storing unit, in which the three-dimensional vessel geometry model is stored already and from which the stored three-dimensional vessel geometry model can be provided.

The rotational position determination apparatus 15 further comprises an inner path providing unit 3 for providing a representation of the inner path 8 within the person 2. In this embodiment, the inner path providing unit 3 is adapted to determine the inner path 8 by determining a path through the provided three-dimensional vessel geometry model from the entry site 5 to the target site 6. The inner path providing unit 3 can, for example, be adapted to determine the shortest path within the person 2, which has a diameter being sufficiently large for moving the insertion device from the entry site 5 to the target site 6. In another embodiment, also the inner path providing unit 3 can be a storing unit, in which the inner path is stored already and from which the inner path can be provided. The inner path providing unit can also be a receiving unit for receiving the inner path via a wired or wireless data connection, wherein the inner path providing unit is adapted to provide the received inner path. Also the three-dimensional vessel geometry model providing unit can be a receiving unit for receiving the three-dimensional vessel geometry model and for providing the received three-dimensional vessel geometry model.

The rotational position determination apparatus 1 further comprises an inner path length determination unit 12 for determining the length of the inner path 8 based on the provided representation of the inner path 8. Since the inner path 8 is known in the three-dimensional vessel geometry model, the inner path 8 can be determined by calculating the length of the inner path 8 within the three dimensional vessel geometry model.

The rotational position determination apparatus 15 further comprises an inner path element selection unit being, in this embodiment, a delivery system selection unit 13 for selecting a delivery system for delivering the insertion device to the target site 6, wherein the delivery system selection unit 13 is adapted to select the delivery system depending on the determined length of the inner path. In this embodiment, the delivery system comprises a guidewire and a delivery unit, wherein the delivery unit is adapted to hold the insertion device and to be moved along the guidewire, in order to deliver the insertion device from the entry site 5 to the target site 6. In FIG. 1, the delivery system is represented by the guidewire 14. The delivery system selection unit 13 can, for example, be adapted to select one or several guidewires having a length which fits to the length of the inner path. For instance, the delivery system selection unit 13 can comprise a data base, in which an assignment between delivery systems and possible lengths of the inner path are stored, wherein a suitable delivery system can be selected from the data base based on the assignments. The delivery system selection unit 13 can also be adapted to select a delivery system based on other characteristics of the inner path like the minimal diameter along the inner path, the location of the inner path, et cetera. The delivery system selection unit 13 is preferentially adapted to not only select the length of the respective guidewire as part of a delivery system, but to also select a delivery unit for delivering the insertion device along the guidewire within the person. The delivery system selection unit can further be adapted to select other endovascular devices, which may be used during the interventional procedure, based on characteristics of the provided representation of the inner path 8.

Figure 2:
FIG. 2 shows schematically and exemplarily an embodiment of an insertion device.
Figure 3:
FIG. 3 shows schematically and exemplarily another embodiment of an insertion device.

The rotational position determination apparatus 15 further comprises a target rotational position providing unit 4 for providing a desired target rotational position of the insertion device at the target site 6. In this embodiment, the insertion device is a fenestrated stent 10 with a window 39 as schematically and exemplarily shown in FIG. 2. The window 39 is provided for allowing the fenestrated stent 10 to be introduced into a branched vessel without closing a branch of the vessel. In another embodiment, the insertion device can also be a two-legged stent 11 as schematically and exemplarily shown in FIG. 3.

The target rotational position providing unit 4 is adapted to determine the target rotational position such that the endovascular device 10 fits to the vessel configuration at the target site 6. In this embodiment, a branch 30 is present at the target site 6. The target rotational position providing unit 4 is adapted to determine the target rotational position of the fenestrated stent shown in FIG. 2 such that the window 39 of the stent 10 is aligned with the opening 31 of the main vessel 32 to the branch vessel 33. The target rotational position providing unit 4 determines a rotational position of a landmark of the insertion device, wherein the landmark is, for example, the window 39 or another marker on the stent. If the delivery unit delivers the insertion device 10 to the target site 6, for example, along a guidewire 14, wherein there is a fixed and known spatial relationship between the insertion device 10 and the delivery unit, also a marker on the delivery unit can be used as a landmark, wherein the rotational position of this landmark can be provided by the target rotation position providing unit 4 for indicating the target rotational position.

In another embodiment, also the target rotational position providing unit can be a storage unit, in which the desired target rotational position of the insertion device at the target site is stored already, wherein the stored desired target rotational position can be retrieved from the storage unit 4 for providing the desired target rotational position. Moreover, the target rotational position providing unit can also be a receiving unit for receiving the target rotational position via a wired or wireless data connection, wherein the desired target rotational position can have been determined automatically or semi-automatically by another unit, or the target rotational position can be input by a user.

The rotation position determination apparatus 15 further comprises an entry rotational position determination unit 7 for determining the entry rotational position such that a navigation of the insertion device 10 from the entry site 5 to the target site 6 along the inner path 8 results in a rotational position of the insertion device 10 at the target site 6 being equal to the target rotational position based on the representation of the inner path and the desired target rotational position. The entry rotational position determination unit 7 can be adapted to simulate the navigation of the insertion device 10 from the entry site 5 to the target site 6 based on the representation of the inner path and the target rotational position for determining the entry rotational position. In particular, the entry rotational position determination unit 7 can be adapted to simulate the trajectory of the delivery unit, which is used for delivering the insertion device 10 from the entry site 5 to the target site 6 through the representation of the inner path, in particular, through the three-dimensional vessel geometry model along the inner path, while keeping track of the orientation of the landmark. The entry rotational position determination unit 7 can be adapted to use a known simulation method like the simulation methods disclosed in, for example, the article "Simulation of guidewire navigation in complex vascular structures" by V. Guilloux et al., Medical Imaging 2006: Visualization, Image-Guided Procedures, and Display, 6141: 14107-14107 (2006), the article "Remote manipulation of guidewire using an virtual reality device" by K. Fukasaku et al., Interventional Neuroradiology, 7: 29-34 Suppl. (1 Dec. 2001); and the article "A real-time interactive surgical simulator for catheter navigation" by Lim et al., Surgical-Assist Systems, Proceedings of SPIE, 3262: 4-14 (1998), which are herewith incorporated by reference. Another known simulation method, which could be used by the entry rotational position determination unit, is disclosed in the article "Development of a training system for interventional radiology" by M. Ide et al., Modelling in Medicine and Biology VIII, 313-322 (2009), which is also incorporated by reference.

In an embodiment, the entry rotational position determination unit 7 can also be adapted to determine the entry rotational position without performing a simulation. For example, if, in an embodiment, the inner path is relatively straight and has a relatively large diameter such that a rotation of the insertion device 10 is not required while being navigated from the entry site 5 to the target site 6, the entry rotational position can be determined as being equal to the target rotational position, or, if it is known from, for instance, a database, that a navigation along the actual inner path requires a rotation of the insertion device 10 by a certain known angle, the entry rotational position can be determined based on the provided target rotational position and the certain known angle, without necessarily performing a simulation.

The rotational positioning assistance apparatus 16 is adapted to assist in positioning the insertion device 10 at the entry site 5. The rotational positioning assistance apparatus 16 comprises an actual entry rotation position determination unit 17 for determining an actual entry rotational position of the insertion device 10 at the entry site 5. In this embodiment, the actual entry rotational position determination unit 17 is adapted to determine the actual entry rotational position of the insertion device 10 at the entry site 5 based on a fluoroscopy image generated by a fluoroscopy apparatus 34. The fluoroscopy apparatus 34 comprises a radiation source 22, in particular, an x-ray source, and a detection unit 23 for detecting the radiation 35 emitted by the radiation source 22 after having traversed the person 2. The fluoroscopy apparatus 34 further comprises a fluoroscopy control unit 24 for controlling the radiation source 22 and the detection unit 23 and for providing the fluoroscopy image to, for example, the rotational positioning assistance apparatus 16. The fluoroscopy apparatus 34 is, for example, a C-arm apparatus.

The landmark on the insertion device 10 is chosen such it is detectable in the fluoroscopy image. In particular, the landmark can be the window 39, which is detectable in the fluoroscopy image, or another mark on the insertion device 10 or on the delivery unit. The actual entry rotational position can therefore be determined by detecting the landmark in the fluoroscopy image.

The rotational position determination apparatus 15 further comprises an entry path providing unit 48 for providing an entry path from the outside of the person 2 to an end of the inner path 8 at the entry site, wherein the entry rotational position determination unit 7 can be adapted to determine the entry rotational position such that the navigation of the insertion device 10 from the entry site 5 to the target site 6 along the entry path and the inner path 8 results in a rotational position of the insertion device at the target site being equal to the target rotational position based on the representation of the entry path, the representation of the inner path and the desired target rotational position. A possible arrangement at the entry site 5 is schematically and exemplarily shown in more detail in FIG. 4.

Figure 4:
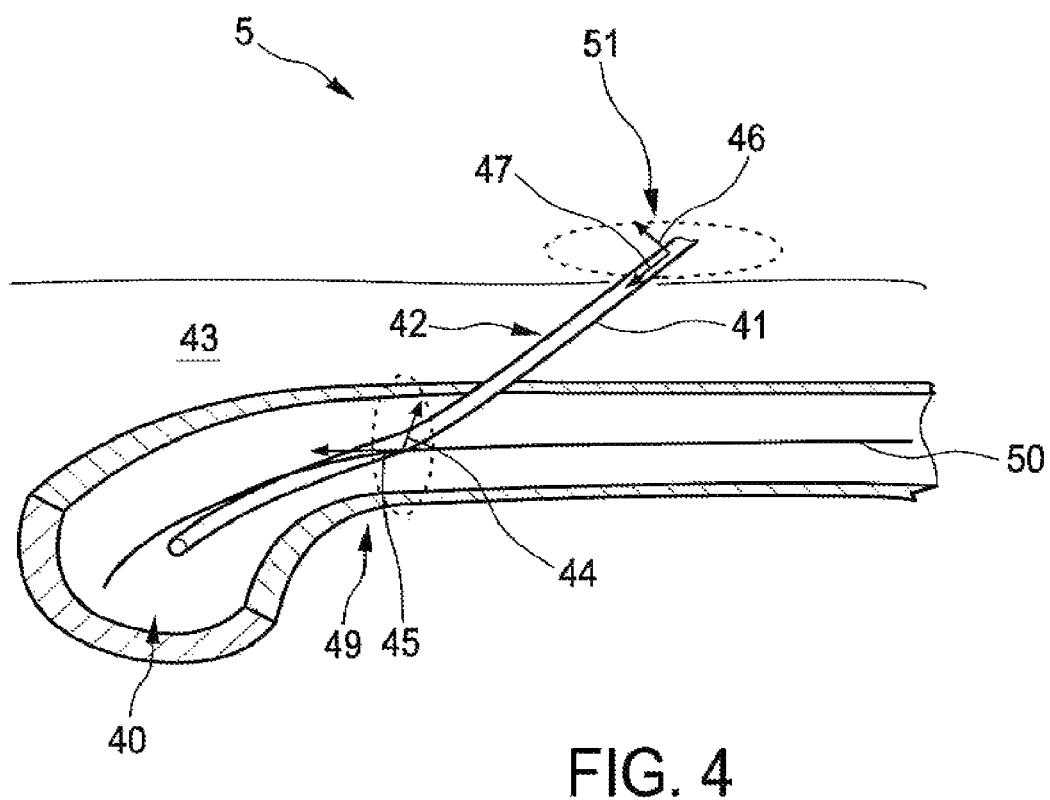
FIG. 4 shows schematically and exemplarily an introducer sheath for providing an access to a femoral artery.

FIG. 4 shows schematically and exemplarily an introducer sheath 41, which has been introduced into a femoral artery 40 through tissue 43, in order to provide an access of the insertion device 10 to the femoral artery 40. The introducer sheath 41 is visible in the fluoroscopy image such that the entry path providing unit 48 can detect the introducer sheath 41 and determine the entry path 42 from the detected introducer sheath 41 for providing the entry path 42. For example, the introducer sheath 41 can comprise markers, which are visible in the fluoroscopy image, in order to determine the entry path based on the fluoroscopy image.

The entry rotational position determination unit 7 can be adapted to firstly determine an intermediate entry rotational position at the end 49 of the inner path 8 such that a navigation of the insertion device 10 from the end 49 to the target site 6 along the inner path 8 results in a rotational position of the insertion device 10 at the target site 6 being equal to the desired target rotational position based on the representation of the inner path 8 and the provided desired target rotational position. The resulting intermediate rotational position 44 is schematically and exemplarily indicated at the end 49 of the inner path 8 with respect to a reference rotational position 45 in a plane being perpendicular to a tangent of the centre line 50 of the femoral artery 40.

Figure 5:
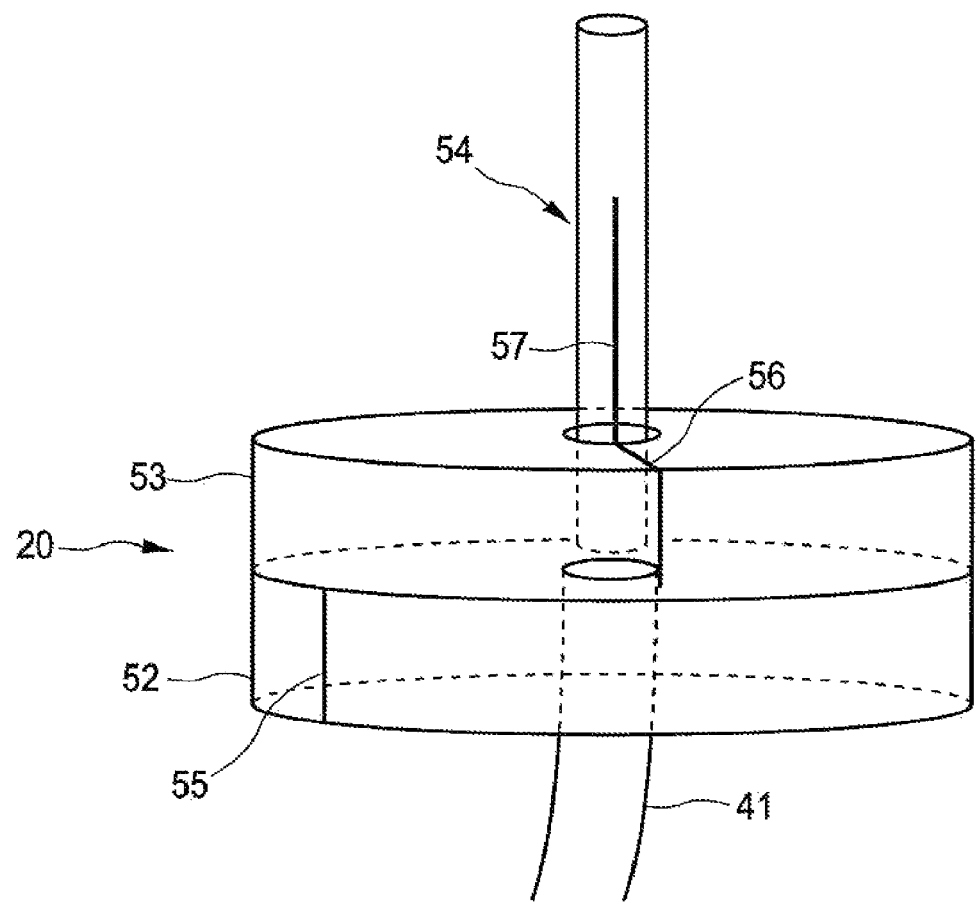
FIG. 5 shows schematically and exemplarily an arrangement for rotating a delivery unit relative to the introducer sheath.

The entry rotational position determination unit 7 can be further adapted to determine the entry rotational position at the outside 51 based on the intermediate entry rotational position 44 and the provided representation of the entry path 42. The resulting final entry rotational position 46 can be determined in a plane being substantially perpendicular to the centre line of the introducer sheath at the entry site 5 and can be calculated with respect to an external reference rotational position 47, which has a known relation with a corresponding internal reference rotational position 45. In particular, the final entry rotational position 46 is preferentially defined in a normal plane being perpendicular to the tangent vector of the centre line of the introducer sheath at the outside 51. If desired, the final entry rotational position can be projected on any other plane, which may not be perpendicular to the tangent vector, except for planes which contain the tangent vector. For example, the final entry rotational position can be projected onto a plane defined by the ring-shaped elements shown in FIG. 5.

If in an embodiment the planes at the end 49 of the inner path 8 and at the outside 51 are both equally oriented with respect to the tangent to the centre line of the introducer sheath 41, for example, perpendicular to the tangent, the reference rotational positions in these planes can be provided such that they describe how a rotational position of the insertion device will be modified, while being moved from the outside location 51 to the inside location 49. Thus, if in this embodiment an intermediate entry rotational position has been determined enclosing an angle α with a reference rotational position at the end 49 of the inner path 8 in a plane having a certain orientation with respect to the tangent to the centre line of the introducer sheath 41, the desired entry rotational position at the outside location 51 can be determined by adding the same angle α to the reference rotational position in a plane having the same certain orientation to the tangent at the outside location 51. The desired entry rotational position at the outside location 51 can be provided in another plane having another orientation by projecting the desired rotational position, which has been determined for the plane having the certain orientation with respect to the tangent at the outside location 51, onto the other plane having the other orientation. Moreover, also the intermediate entry rotational position at the end 49 of the inner path 8 can firstly be provided in a plane having an orientation being different to the certain orientation with respect to the tangent at the end 49 of the inner path 8, wherein the intermediate entry rotational position can be projected onto the plane having the certain orientation with respect to the tangent to the centre line of the introducer sheath 41. In general the intermediate entry rotational position at the end 49 of the inner path 8 and the desired entry rotational position at the outside 51 can be provided in differently oriented planes.

The rotational positioning assistance apparatus 16 further comprises a deviation calculation 18 for calculating a deviation between the actual entry rotational position and the desired entry rotational position determined by the entry rotational position determination unit 7 and an indication unit 19 for indicating a desired entry rotational position at the entry site 5 determined by the entry rotational position determination unit 7. In particular, the indication unit 19 is a display showing the entry rotational position. In this embodiment, the indication unit 19 is adapted to indicate the desired entry rotational position by indicating the deviation calculated by the deviation calculation unit 18. The indication unit 19 can show a text advising the user to rotate the insertion device by a certain rotational angle in a certain rotational direction as defined by the calculated deviation. In addition or alternatively, the indication unit 19 can show a graphical tool representing the calculated deviation like a cartoon with the correct orientation of the insertion device 10 relative to the actual entry rotational position or an arrow. The deviation can also be shown as a graphical overlay on top of the fluoroscopy image, for example, similar in principle to the overlay image provided by the three-dimensional image needle guidance system XperGuide of the company Philips.

The rotational positioning apparatus 20 is adapted to position the insertion device 10 at the entry site 5. The rotational positioning apparatus 20 is not shown in FIG. 4 for clarity reasons, i.e. in order to clearly show the relation between the rotational positions at the ends of the entry path. However, an embodiment of the rotational positioning apparatus 20 is exemplarily and schematically shown in more detail in FIG. 5.

The rotational positioning apparatus 20 comprises two ring-shaped elements 52, 53, which are movable with respect to each other. A first ring-shaped element 52 can be fixed to the person 2 by using a fixation system like a belt, glue, et cetera. Moreover, the first ring-shaped element 52 is fixed with respect to the introducer sheath 41. A second ring-shaped element 53 encloses a delivery unit 54 or, if a delivery unit is not used, the insertion device, wherein the delivery unit 54 can temporarily be fixed to the second ring-shaped element 53, in order to rotate the delivery unit 54 with respect to the introducer sheath 41 by moving the second ring-shaped element 53 with respect to the first ring-shaped element 52. The rotational positioning apparatus 20 can be adapted to allow a user to manually rotate the second ring-shaped element 53 with respect to the first ring-shaped element 52 and/or the rotational positioning apparatus 20 can be adapted to rotate the second ring-shaped element 53 with respect to the first ring-shaped element 52 by using one or several motors included in at least one of the first and second ring-shaped elements 52, 53. The delivery unit 54 or, if the insertion device is inserted without using the delivery unit 54, the insertion device 10 can be temporarily fixed to the second ring-shaped element 53 by using fixation elements like screws, which can be moved radially, in order to hold the delivery unit 54 at a fixed position with respect to the second ring-shaped element 53. Alternatively or in addition, at least around the opening of the ring-shaped element 53 the second ring-shaped element 53 can be made of an elastic material like, for example latex, in order to temporally hold the delivery unit 54 at a fixed position with respect to the second ring-shaped element 53. The indication unit 19 can indicate the correct desired entry rotational position such that a user can rotate the delivery unit 54 to the correct desired entry rotational position by rotating the second ring-shaped element 53 with respect to the first ring-shaped element 52. Alternatively or in addition, indications for indicating the correct desired entry rotational position can also be provided on the rotational positioning apparatus 20. For example, indications 55 and 56 can be provided on the first and second ring-shaped elements 52, 53, respectively, wherein at least one of these indications 55, 56 can be movable with respect to the respective first or second ring-shaped element 52, 53, in order to allow the rotational positioning apparatus 20 to indicate the correct desired entry rotational position. For example, one of these indications 55, 56 can be provided by light-emitting diodes distributed over the circumference of the respective ring-shaped element.

The delivery unit 54 can comprise an indication 57, wherein a user can align the indications 57 and 56, in order to arrange the delivery unit 54 within the upper ring-shape element 53 in a known rotational position with respect to the upper ring-shaped element 53. Thus, in an embodiment the rotational position determination apparatus can be adapted to determine the positions and orientations of the different elements, except for the delivery unit 54, with respect to a reference system by using, for example, a fluoroscopy image showing the introducer sheath 41 and the ring-shaped elements 52, 53 and by registering the fluoroscopy image with a pre-operatively acquired image, which has been used for determining the inner path. The rotational position of the delivery unit 54 with respect to the reference system can then be determined by arranging the delivery unit 54 within the ring-shaped element 53 such that the indications 57 and 56 are aligned. However, in another embodiment the fluoroscopy image can also show the delivery unit 54 such that the rotational position of the delivery unit 54 can be determined with respect to the reference system, without aligning the indications 56 and 57.

The rotational positioning apparatus 20 can be connected to the rotational positioning assistance apparatus 16, in order to allow the rotational positioning apparatus 20 to rotate the insertion device 10 to the correct rotational position based on the calculated deviation. In another embodiment, the rotational positioning apparatus can have another construction for rotating the insertion device, in particular, for rotating a delivery unit comprising the insertion device, for positioning the insertion device in the correct entry rotational position at the entry site.

After the insertion device 10 has been rotated to the correct entry rotational position, the insertion device 10 is navigated to the target site 6, for example, by using a delivery system. Since the insertion device has been arranged at the correct entry rotational position, the insertion device 10 is also correctly oriented at the target site 6. In particular, at the target site 6 the window 39 of the stent 10 is aligned with the opening 31 from the main vessel 32 to the branch vessel 33.

Figure 6:
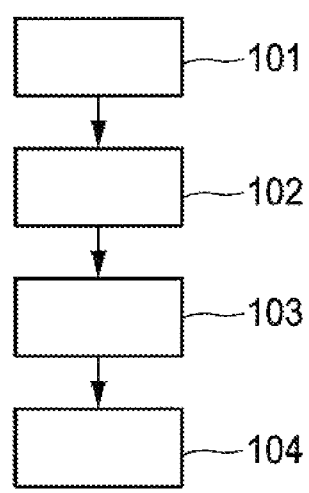
FIG. 6 shows a flowchart exemplarily illustrating an embodiment of a rotational position determination method for determining an entry rotational position.

FIG. 6 shows a flowchart exemplarily illustrating an embodiment of a rotational position determination method for determining a rotational position of an insertion device for being inserted into an object at an entry site and for being navigated along an inner path within the object to a target site within the object.

In step 101, the representation of the inner path within the object is provided by the inner path providing unit 3. The inner path can be provided by, for example, providing a three-dimensional vessel geometry model representing a vascular network of the object and by determining a path through the three-dimensional vessel geometry model from the entry site to the target site. In step 102, a desired target rotational position of the insertion device at the target site is provided by the target rotational position providing unit 4. In particular, the target rotational position providing unit 4 determines the target rotational position such that the insertion device fits to the vessel configuration at the target site. In step 103, the entry rotational position is determined such that a simulation of the navigation of the insertion device from the entry site to the target site along the representation of the inner path results in a rotational position of the insertion device at the target site being equal to the target rotational position by the entry rotational position determination unit 7.

In step 104, the determined entry rotational position at the entry site is indicated by the indication unit 19. In particular, the actual entry rotational position determination unit 17 can determine the actual entry rotational position of the insertion device at the entry site, the deviation calculation unit 18 can calculate a deviation between the actual rotational position and the determined desired entry rotational position, wherein the indication unit 19 can indicate the entry rotational position by indicating the deviation. In step 104, alternatively or in addition, the insertion device can be positioned at the entry site in the correct entry rotational position by using the rotational positioning apparatus 20.

In step 103, an entry rotational position can be determined at the outside of the person 2 at the entry site by considering the representation of the inner path and a representation of an entry path as described above. Moreover, in step 103 instead of using a simulation the entry rotational position can be determined in another way, for example, by using a data base providing changes of the rotational position obtained while navigating the insertion device along the inner path and optionally along the entry path depending on characteristics of the inner path and optionally the entry path determined from the respective representations.

The above described apparatus is a method which may be adapted to be used for the treatment of abdominal aortic aneurism (AAA) and of thoracoabdominal aortic aneurism (TAAA), wherein fenestrated (two)-legged stents or multi-branched stents may be implanted. The correct positioning of such stents in relation to the patient-specific aortic anatomy is of extreme importance. In the case of a fenestrated stent, the apertures of the stent have to be correctly aligned with the corresponding aortic side branches and no important side branch should be covered. In the case of branched stents, the branches of the stent have to correctly match the aortic branches.

The rotational position determination apparatus, the rotational positioning assistance apparatus and/or the rotational positioning apparatus are preferentially adapted to be used for performing a stenting procedure involving inserting a guidewire, for example, through the femoral artery, which serves as a monorail to guide the insertion device, in particular, a stent delivery unit with the insertion device, and optionally any other needed devices such as angioplasty balloons, from the entry site to the target site.

Most available delivery units used to deploy such stents have limited or no possibility of being rotated after they arrive at their deployment position which implies that they should be inserted with the (near) correct angle so that, when deployed, landmarks (for example, apertures, in the case of fenestrated stents, or branches, in the case of branched stents) will be aligned with the appropriate vessels. If this is not achieved in the first try, it may be necessary to retrieve, rotate and reinsert the delivery unit until the desired alignment is obtained.

Since the above described rotational position determination apparatus and method determines a correct entry rotational position of the insertion device, the need of re-insertions due to wrong alignment can be reduced. Ideally, a re-insertion is not needed at all, because, if the insertion device is arranged at the correct rotational position at the entry site, the insertion device is also in the correct rotational position at the target site. In order to determine the correct rotational position at the target site, the rotational position determination apparatus and method can be adapted to keep track of the angular orientation of the insertion device, in particular, of the delivery unit comprising the insertion device, during a simulation of the trajectory through the segmented model of the vascular network of the person. The rotational position determination apparatus and method can be adapted to be used independently of a delivery system choice.

The rotational position determination apparatus and method can be adapted to determine the entry rotational position pre-operatively or just before an intervention.

The rotational position determination apparatus and method can be adapted to be used in interventional x-ray. The rotational position determination method can be implemented in software, wherein the software can be implemented in, for example, XtraVision platform of the company Philips, or as a stand-alone application targeted for stent (-graft) planning. The rotational position determination apparatus 15, the rotational positioning assistance apparatus 16 and the rotational positioning apparatus 20 can each be regarded as being an independent device, which can be an accessory for interventional x-ray systems.

The rotational position determination apparatus, the rotational positioning assistance apparatus and the rotational positioning apparatus can be regarded as being separate apparatuses, or they can be regarded as being comprised by a single apparatus. For example, the rotational position determination apparatus can comprise the rotational positioning assistance apparatus and/or the rotational positioning apparatus.

The above-mentioned introducer sheath is preferentially rigid, i.e. maintains its form, and has preferentially special marks in the part that will be introduced into the person at the entry site, in particular, that will be introduced into the femoral artery. The special marks are positioned in such a way that it is possible to register the angular positioning of the introducer sheath with respect to the three-dimensional image obtained pre-operatively for determining the representation of the inner path. The finally determined desired entry rotational position may be indicated on the exterior of the introducer sheath, i.e. the exterior of the introducer sheath may comprise the indication unit.

In another embodiment, after the introducer sheath has been introduced, the three-dimensional image obtained pre-operatively can be registered with the fluoroscopy image, wherein the markers of the introducer sheath can be used to register the angular positioning of the introducer sheath with respect to the three-dimensional image obtained pre-operatively. The registration result yields the entire path from the outside of the person at the entry site to the target site including the entry path and the inner path, thereby allowing to determine the correct entry rotational position at the outside of the person at the entry site, in particular, with respect to an introducer exterior plane.

In a further embodiment, a specially marked catheter can be used, which can be adapted to be inserted into the femoral artery in order to achieve the alignment, i.e. in order to arrange the insertion device at the entry site in the correct rotational entry position. The desired entry rotational position could, for example, be marked on an introducer sheath, through which the catheter may be inserted into the person, or on a leg of the person in case no introducer sheath is used or in an external apparatus that can be attached to an existing introducer sheath.

In a further embodiment, after the introducer sheath has been introduced, a three-dimensional image of the entry site can be generated by using, for example, rotational x-ray. The three-dimensional image can be aligned with and registered to the image of the vascular three used for determining the representation of the inner path. After this registration has been performed, the entire path including the inner path and the entry path are defined such that the entry rotational position at the outside of the person at the entry site, in particular, with respect to an introducer plane at the outside of the person, can be determined, for example, by simulating the trajectory of the insertion device or of a delivery unit holding the insertion device from the introducer entry, i.e. from the outside of the person at the entry site, to the target site. In particular, firstly an intermediate entry rotational position can be determined at the end of the inner path at the entry site and then the final entry rotational position at the outside of the person at the entry site can be determined based on the representation of the entry path and the intermediate entry rotational position. Alternatively, instead of a three-dimensional image of the introducer site two orthogonal images can be acquired and used for the aligning and registration procedure.

Although in an above described embodiment an indication unit 19 for indicating an entry rotational position at the entry site is part of the rotational positioning assistance apparatus 16, in other embodiments the indication unit can also be a separate unit or can be a part of another unit or apparatus. For example, the rotational positioning apparatus 20, in particular, the introducer, can comprise a display for indicating the correct entry orientation of the insertion device or of the delivery unit, if the insertion device is held by the delivery unit, at the entry site by means of, for instance, a rotating arrow, light, et cetera. As already mentioned above, the indication unit can also be a separate unit, which can be attached to an existing introducer sheath, wherein the indication unit can comprise a display for indicating the correct entry rotation position of the insertion device and/or of the delivery unit by means of, for instance, a rotating arrow, light, et cetera.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of an inner path, the determination of a target rotational position, the determination of an entry rotational position et cetera performed by one or several units or devices can be performed by any other number of units or devices. The determinations and/or the control of the rotational position determination apparatus in accordance with the rotational position determination method and/or the control of the rotational positioning assistance apparatus in accordance with the rotational positioning assistance method and/or the control of the rotational positioning apparatus in accordance with the rotational position determination method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a rotational position determination apparatus for determining an entry rotational position, which defines a rotational position of an insertion device like a stent at an entry site, such that a navigation of the insertion device from the entry site to a target site along an inner path results in a rotational position of the insertion device at the target site being equal to a desired target rotational position based on a representation of the inner path and the desired target rotational position. If the insertion device is arranged in the determined entry rotational position at the entry site and then navigated to the target site, it is therefore not necessary to rotate the insertion device at the target site, i.e. it is not necessary to use a technically complex interventional device for rotating the insertion device at the target site.

The invention claimed is:

1. A rotational positioning assistance apparatus for assisting in positioning an insertion device for being inserted into an object at an entry site and for being navigated along an inner path within the object to a target site within the object, wherein the rotational positioning assistance apparatus comprises an indication unit for indicating a desired entry rotational position at the entry site determined by a rotational position determination apparatus, said rotational position determination apparatus configured to determine a rotational position of the insertion device for being inserted into the object and for being navigated along an inner path within the object from the entry site to the target site within the object, the rotational position determination apparatus comprising a computer and a memory with instructions that, when executed by the computer, configure the computer to:
provide a representation of the inner path within the object,
provide a desired target rotational position of the insertion device at the target site,
determine an entry rotational position, which defines a rotational position of the insertion device at the entry site, such that a navigation of the insertion device from the entry site to the target site along the inner path results in a rotational position of the insertion device at the target site being equal to the desired target rotational position based on the representation of the inner path and the desired target rotational position, and
provide an output for indicating the determined entry rotational position.

2. A rotational positioning apparatus for positioning an insertion device for being inserted into an object at an entry site and for being navigated along an inner path within the object to a target site within the object, wherein the rotational positioning apparatus comprises a positioning unit for positioning the insertion device at the entry site in an entry rotational position determined by a rotational position determination apparatus, the rotational position determination apparatus comprising a computer and a memory with instructions that, when executed by the computer, configure the computer to:
provide a representation of the inner path within the object;
provide a desired target rotational position of the insertion device at the target site;
determine an entry rotational position, which defines a rotational position of the insertion device at the entry site, such that a navigation of the insertion device from the entry site to the target site along the inner path results in a rotational position of the insertion device at the target site being equal to the desired target rotational position based on the representation of the inner path and the desired target rotational position; and
provide an output for indicating the determined entry rotational position.

3. A rotational positioning assistance method for assisting in positioning an insertion device for being inserted into an object at an entry site and for being navigated along an inner path within the object to a target site within the object, wherein the rotational positioning assistance method comprises indicating a desired entry rotational position at the entry site, which is determined by a rotational position determination method, the rotational position determination method comprising:
providing a representation of the inner path within the object by a computer;
providing a desired target rotational position of the insertion device at the target site by the computer;
determining an entry rotational position, which defines a rotational position of the insertion device at the entry site, such that a navigation of the insertion device from the entry site to the target site along the inner path results in a rotational position of the insertion device at the target site being equal to the desired target rotational position based on the representation of the inner path and the desired target rotational position by the computer; and
providing by the computer an output for indicating the determined entry rotational position by an indication unit.

4. A rotational positioning method for positioning an insertion device for being inserted into an object at an entry site and for being navigated along an inner path within the object to a target site within the object, wherein the rotational positioning method comprises positioning the insertion device at the entry site in an entry rotational position, which is determined by a rotational position determination method comprising:
providing a representation of the inner path within the object by a computer;
providing a desired target rotational position of the insertion device at the target site by the computer;

determining an entry rotational position, which defines a rotational position of the insertion device at the entry site, such that a navigation of the insertion device from the entry site to the target site along the inner path results in a rotational position of the insertion device at the target site being equal to the desired target rotational position based on the representation of the inner path and the desired target rotational position by the computer; and providing by the computer an output for indicating the determined entry rotational position, by a rotational positioning apparatus as defined in claim 2.

5. A system characterized in that the system comprises:

a rotational position determination apparatus for determining a rotational position of an insertion device for being inserted into an object and for being navigated along an inner path within the object from an entry site to a target within the object, the rotational position determination apparatus comprising a computer and a memory with instructions that, when executed by the computer, configure the computer to:

provide a representation of the inner path within the object, provide a desired target rotational position of the insertion device at the target site, determine an entry rotational position, which defines a rotational position of the insertion device at the entry site, such that a navigation of the insertion device from the entry site to the target site along the inner path results in a rotational position of the insertion device at the target site being equal to the desired target rotational position based on the representation of the inner path and the desired target rotational position, and provide an output for indicating the determined entry rotational position;

a rotational positioning assistance apparatus for assisting in positioning the insertion device at the entry site; and a rotational positioning apparatus for positioning the insertion device at the entry site.

\* \* \* \* \*